United States Patent
Wu

[11] Patent Number: 5,837,821
[45] Date of Patent: Nov. 17, 1998

[54] ANTIBODY CONSTRUCT

[75] Inventor: Anna M. Wu, Sherman Oaks, Calif.

[73] Assignee: City of Hope, Duarte, Calif.

[21] Appl. No.: 256,156

[22] PCT Filed: Nov. 4, 1992

[86] PCT No.: PCT/US92/09347

§ 371 Date: Jun. 24, 1994

§ 102(e) Date: Jun. 24, 1994

[87] PCT Pub. No.: WO94/09817

PCT Pub. Date: May 11, 1994

[30]    Foreign Application Priority Data

Nov. 4, 1992 [WO]    WIPO .............. PCT/7S92/09347

[51] Int. Cl.[6] .................. C07K 16/46; C12N 15/10; C07H 21/04
[52] U.S. Cl. .................. 530/387.3; 530/387.7; 530/866; 530/867; 435/69.7; 435/320.1; 435/252.3; 435/252.33; 435/328; 536/23.53
[58] Field of Search ................ 530/387.3, 387.7, 530/866, 867; 435/69.7, 240.1, 320.1, 252.3, 252.33

[56]    References Cited

FOREIGN PATENT DOCUMENTS 0506124   9/1992   European Pat. Off. .

OTHER PUBLICATIONS

Neumaier et al. [Cancer Research 50:2128–2134 (1990)].
Pack et al. [Biochemistry 31(6):1579–1584 (1992)].
Mueller et al. [Immunology 87:5702–5705 (1990)].
Colcher et al., *Journal of the National Cancer Institute*, 82:14, pp. 1191–1197 (1990).
Cumber et al., *Journal of Immunology*, 149:1, pp. 120–126 (1992).
Hu et al., *Cancer Research*, 56:13, pp. 3055–3061 (1996).

*Primary Examiner*—Frank C. Eisenschenk
*Attorney, Agent, or Firm*—Rothwell, Figg, Ernst & Kurz

[57]    ABSTRACT

An antigen binding protein construct or "minibody" which includes the VL and VH domains of a native antibody fused to the hinge region and CH3 domain of the immunoglobulin molecule is described. Minibodies are small versions of whole antibodies which encode in a single chain the essential elements of a whole antibody. Minibodies are expressed by host cells transformed with minibody genes.

19 Claims, 3 Drawing Sheets

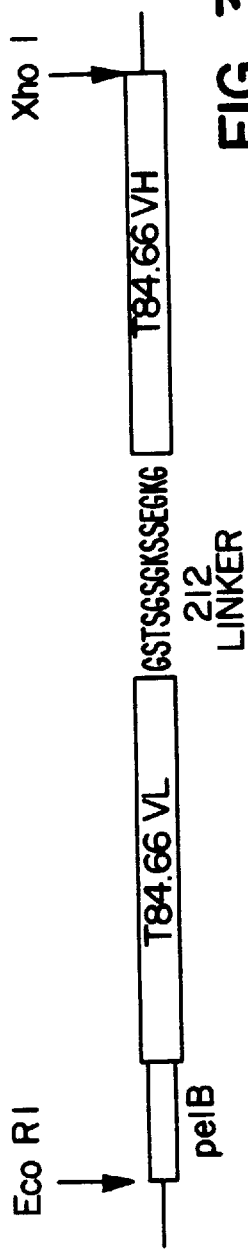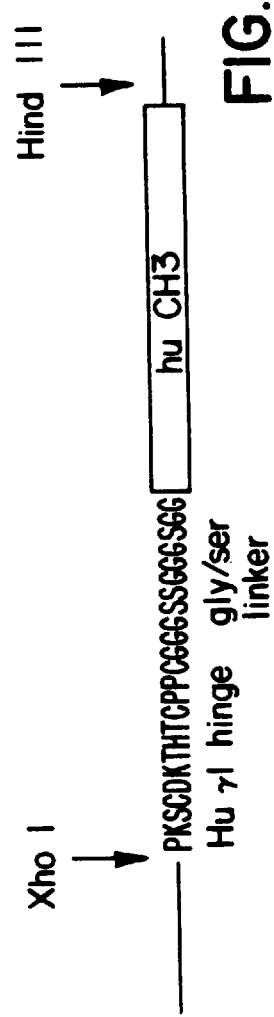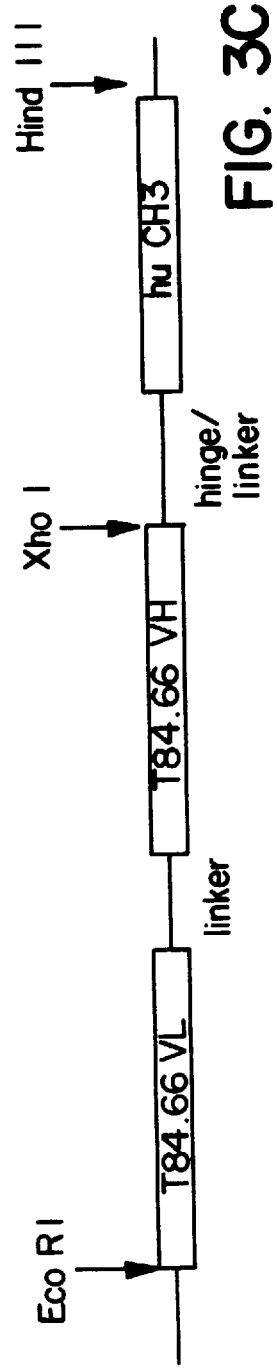

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

Gly Ser Thr Ser Gly Ser Gly Lys Ser Ser Glu Gly Lys Gly
1               5                   10

( 2 ) INFORMATION FOR SEQ ID NO:2:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:2:

Pro Lys Ser Cys Asp Lys Thr His Thr Cys Pro Pro Cys Gly Gly
1               5                   10                  15

Gly Ser Ser Gly Gly Gly Ser Gly Gly
                20

ANTIBODY CONSTRUCT

This invention was made with government support under Grant Nos. P01CA43904 and R01CA42329 awarded by the National Institutes of Health. The government has certain rights in the invention.

This application is a National Stage Application of PCT/US92/09347, filed 04 Nov. 1992.

FIELD OF INVENTION

This invention relates to a novel antigen binding protein construct or "minibody" which includes the essential elements of an antibody.

BACKGROUND OF THE INVENTION

Previous workers (1)[1]/have demonstrated that single chain antigen-binding proteins can be generated by linking the heavy chain variable domain and light chain variable domain of an antibody into a single protein, using a short linker peptide. The length and composition of the linker can vary (2). Single chain antibodies can be produced in E. coli which retain antigen-binding activity. Milenic (3) provides one recent example of a single chain antibody that binds a tumor antigen. Several other single chain antibodies generated that bind to various haptens and antigens have been reported.

[1]/Reference citations appear in the bibliography.

Gillies and Wesolowski (4) demonstrated that the CH2 domain of antibodies can be deleted with retention of the antigen binding function. The CH3 domains of such ΔCH2 antibodies permit dimerization. ΔCH2 antibodies are useful for in vivo diagnostics and potentially therapy (5).

To produce bispecific antibodies, Kostelny et al (6) fused Fab fragments of antibodies to the leucine zipper portions of fos and jun proteins in the absence of a single chain construct for the antigen combining region. Pack and Pluckthun (7), fused a single chain antibody to amphipathic helices from a four helix bundle or from leucine zipper proteins.

SUMMARY OF THE INVENTION

Minibodies are engineered antibody constructs comprised of the variable heavy (VH) and variable light (VL) chain domains of a native antibody fused to the hinge region and to the CH3 domain of the immunoglobulin molecule. Minibodies are thus small versions of whole antibodies encoded in a single protein chain which retain the antigen binding region, the CH3 domain to permit assembly into a bivalent molecule and the antibody hinge to accommodate dimerization by disulfide linkages. In contrast, native antibodies are comprised of four chains, two heavy and two light.

The size, valency and affinity of the minibody is particularly suited for in vivo targeting. Expression in bacterial or mammalian cells is simplified because minibodies are in single chains.

DESCRIPTION OF THE FIGURES

FIG. 3 depicts the construction of a minibody gene (SEQ ID NO:1 and SEQ ID NO:2).

DETAILED DESCRIPTION OF THE INVENTION

Figure 1:
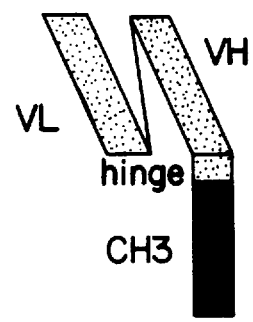
FIG. 1 depicts one form of a minibody in which VL indicates the variable light chain domain and VH indicates the variable heavy chain domain of a native T84.66 antibody. The hinge and CH3 domain are from human IgG.
Figure 2:
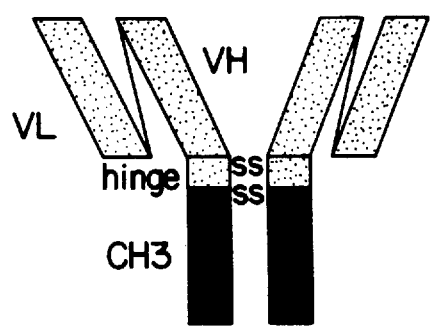
FIG. 2 depicts a dimerized minibody.

A minibody is a chimeric molecule, typically illustrated by FIG. 1, constructed by fusion of a single chain antibody to the hinge region of an antibody followed directly by the CH3 domain of the immunoglobulin molecule. Two minibodies may dimerize through disulfide linkages as shown by FIG. 2.

The Single Chain Antibody

Single chain antibodies are prepared in the manner described by Bird (1), Pantoliano (2), Milenic (3), or Takkinen (8).

EXAMPLE I

A. The Single Chain T84.66 Antibody

This Example demonstrates the production of a single chain construct derived from the T84.66 antibody depicted by FIG. 3A (SEQ ID NO:1) in Neumaier, M., et al. *Cancer Research* 50:2128–2134 (1990) (10).

The T84.66 antibody domains were assembled in order VL-peptide linker-VH. The 14 amino acid peptide linker was identical to the "212 linker" described in Pantoliano et al. *Biochemistry* 30:10117 (1991) (2). The 14 amino acid linker is represented by SEQ ID NO:1 (GSTSGSGKSSEGKG).

The construction was accomplished by polymerase chain reaction/splice overlap extension (PCR/SOE). See Horton (9). The heavy and light chain gene segments from T84.66 were amplified separately using long overlapping primers that encoded the desired 14 amino acid linker. In addition, bacterial pelB peptide was added upstream from VL. These regions were overlapped and the entire construct was fused by amplification in a secondary PCR reaction. The primer used for amplifying the C-terminus of VH included an XhoI restriction site to accommodate assembly of the minibody. See FIG. 3A (SEQ ID NO:1).

The single chain construct was transferred into the plasmid pUC18 for DNA sequence analysis, and thereafter into the bacterial expression vector pKKtac (see Takkinen (8)). The expression vector was transfected into *E. coli* RV308 for expression. Cultures were grown in rich medium at 37° to an O.D.$_{600}$ of 0.8. Isopropyl thiogalactoside (IPTG) was added to 1 mM to induce synthesis of the single chain antibody. Cultures were then shifted to lower temperature (25° or 30°), and synthesis was allowed to proceed for five hours or overnight.

Because the expression vector includes the pelB signal sequence, the single chain antibody is processed and secreted into the supernatant. CEA-binding activity was detected in the supernatant using a competition ELISA, with murine T84.66 as a standard. Under the best conditions (synthesis at 25°, overnight incubation), CEA-binding activities of 2–5 µg/ml were routinely achieved.

Either affinity chromatography, or a combination of ammonium sulfate precipitation, ion-exchange chromatography, and size fractionation yields pure single chain antibody. A 28K band is seen on silver stained SDS-polyacrylamide gels, and the appropriate size peak is also detected by electrospray mass spectrometry. CEA-binding activity copurifies with the 28K species.

B. Design and Assembly of the Hinge and CH3 Minibody Components

In addition to the single chain antibody, the minibody construct includes the hinge and CH3 domains from an immunoglobulin molecule. Examination of the 3-D structure of the human IgG 1 antibody indicates that the native hinge peptide may be too short to span the distance between the N-termini of the CH3 domains, when the CH2 domain has been deleted. Accordingly, a ten amino acid sequence of glycine and serine residues was added to the hinge and CH3. See FIG. 3B (SEQ ID NO:2).

Assembly of the human IgG 1 hinge region and CH3 domains were accomplished by the polymerase chain reaction/splice overlap extension method. See Horton (9). The overlapping primers used to generate the fusion also encoded the additional ten amino acid glycine/serine linker. Furthermore, the flanking primers incorporated an Xho I site on the 5' end and a Hind III site on the 3' end of the hinge-CH3 segment. See FIG. 3B (SEQ ID NO:2). These restriction sites were added to facilitate cloning and construction of the minibody. The hinge-CH3 construct was subcloned into pUC18, and DNA sequence analysis confirmed the correct sequence had been assembled.

C. The Final T84.66 Minibody Construct

The single chain minibody (including the pelB leader region) and the hinge-CH3 components were isolated from their separate pUC18 plasmids as Eco RI-Xho I and Xho I-Hind III restriction fragments, respectively. The Xho I sites were ligated, and the resulting Eco RI-Hind III minibody gene was recloned into pUC18 to provide a T84.66 minibody. See FIG. 3C. Correct assembly was verified by restriction digestion and DNA sequence analysis.

EXAMPLE II

Expression of the T84.66 Minibody

The entire T84.66 minibody gene construct described in Example I was transferred as an Eco RI-Hind III restriction fragment into the bacterial expression vector pKKtac (8) as described above. The resulting plasmid was transfected into E. coli RV308 for minibody expression.

Pregrowth and induction with IPTG carried out as described in Example IA. Following induction, protein synthesis was allowed to occur at 26° C. for 3 to 20 hours. A competition assay was performed to measure the expression of soluble, secreted minibody in the bacterial supernatants. Titer plate assay wells were coated with CEA, blocked, and sample supernatants were allowed to bind. Murine T84.66 was added as competitor. The extent of competition was determined by ELISA with the result shown by FIG. 4.

Figure 4:
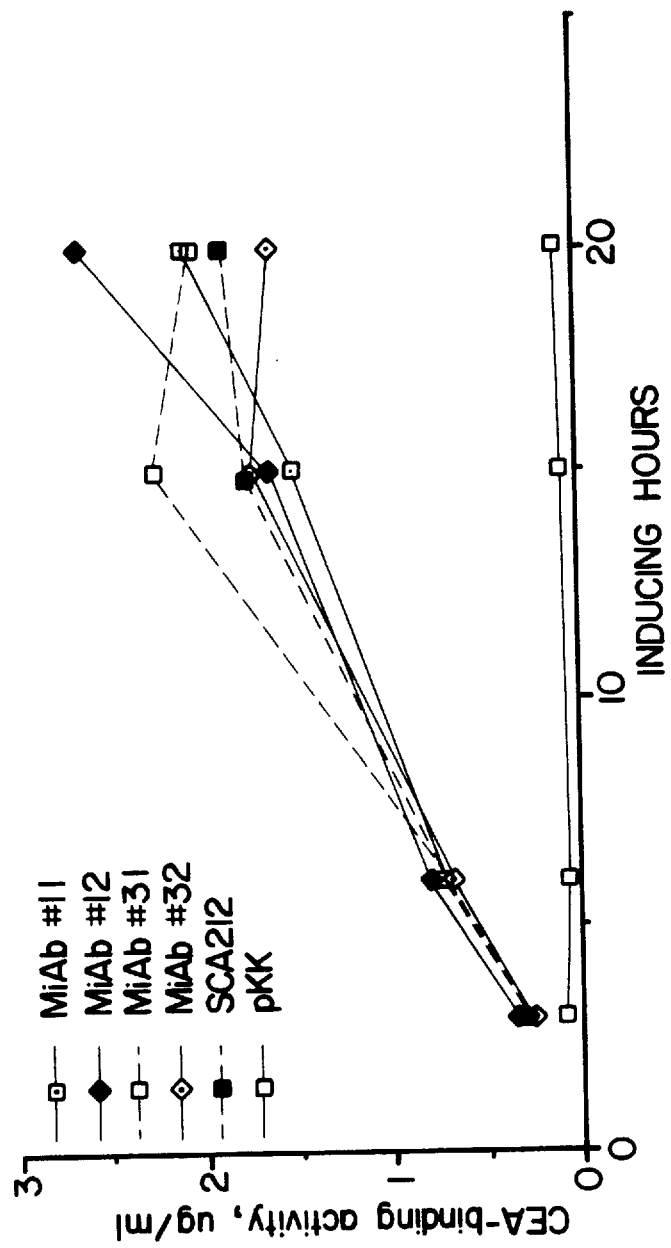
FIG. 4 depicts CEA binding ability of the expression of the product of a T84.66 minibody.

FIG. 4 demonstrates that four independent clones of E. coli RV308 transformed with the minibody expression plasmid (MiAb #s 11, 12, 31 and 32) as well as the single chain antibody (SCA212) yield an expression product having CEA-binding activity. Activities reached >2 µg/ml in the culture supernatants in this experiment. Control cultures (pKK) were negative.

Three lines of evidence indicate that the minibody described in Example II assembles into dimers.

First, a valency greater than one is indicated by an ELISA valency assay. Assay plates were coated with CEA, the minibody sample is added and allowed to bind to the CEA, and the plates are washed. The immobilized minibody was then incubated with biotinylated-CEA. If the minibody is bivalent, it can capture the second CEA molecule and score positive in a color reaction, which it did. Thus, the minibody is at least bivalent.

Second, a native gel shows that the cultures induced to secrete minibody produce a 80–90K protein in the culture supernatant. This protein is apparently the T84.66 minibody.

Third, gel-filtration high-performance liquid chromatography (HPLC) indicates that the CEA-binding activity of the minibody elutes as a single peak, and the apparent molecular weight is between the IgG (150K) and albumin (68K) standards.

The minibody dimer has an appropriate molecular weight for in vivo imaging and therapy studies, it is bivalent for higher affinity, and it demonstrates the feasibility of bispecific minibodies which concurrently bind two different ligands.

BIBLIOGRAPHY

1. Bird et al. *Science* 242:423 (1988)
2. Pantoliano et al. *Biochemistry* 30:10117 (1991)
3. Milenic et al. *Cancer Research* 51:6363 (1991)
4. Gillies and Wesolowski, *Human Antibodies and Hybridomas* 1:47 (1990)
5. Mueller et al. *Proc. Nat. Acad. Sci.* 87:5702 (1990)
6. Kostelny et al, *J. Immunology* 148:1547 (1992)
7. Pack and Pluckthun, Abstract presented at Second Annual IBC International Conference on Antibody Engineering, Dec. 16–18, 1991, San Diego
8. Takkinen, et al. *Protein Engineering* 4:837–841 (1991)
9. Horton, et al. *Gene* 77:61–65 (1989)
10. Neumaier, M., et al. *Cancer Research* 50:2128–2134 (1990)

I claim:

1. A minibody dimer as depicted by FIG. 2.

2. A minibody consisting essentially of the light and heavy chain variable domains of a native antibody fused to hinge and CH3 domains of an immunoglobulin molecule as depicted by FIG. 1.

3. The minibody consisting essentially of the light and heavy chain variable domains of the T84.66 CEA antibody fused to the hinge and CH3 domains of human IgG.

4. The T84.66 minibody depicted by FIG. 3C.

5. *E. coli* RV308 transformed with a plasmid having an expression vector containing the nucleic acid sequence of a minibody gene as defined by claim 4.

6. A method for constructing a minibody as depicted by FIG. 1, which comprises:

(i) providing a single chain antibody including the variable light chain and variable heavy chain domains of a native antibody, and (ii) fusing said single chain antibody to a construct of a native antibody hinge region and CH3 domain.

7. A method as defined by claim 6 in which said native antibody is a CEA antibody.

8. A method as defined by claim 6 in which said native antibody is T84.66 CEA antibody.

9. A method as defined by claim 6 in which said antibody is T84.66 antibody to CEA and in which said hinge region and CH3 domain are the human IgG hinge region CH3 domain.

10. The single chain T84.66 CEA antibody depicted by FIG. 3A (SEQ ID NO:1).

11. A method of producing a minibody depicted by FIG. 1 or FIG. 2 which comprises transforming a host cell with an expression vector containing the nucleic acid sequence of a minibody gene and culturing the transformed host cell under conditions which permit expression of said nucleic acid sequence by said host cell.

12. A method of producing a T84.66 minibody as depicted by FIG. 3C which comprises transforming a host cell with an expression vector containing the nucleic acid sequence of said minibody and culturing the transformed host cell under conditions which permit expression of said nucleic acid sequence by the host cell.

13. A method as defined by claim 12 in which said host cell is *E. coli*.

14. A minibody produced by the method of claim 11 or claim 12.

15. A minibody consisting essentially of the light and heavy chain variable domains of an antibody fused to, in sequence, the hinge region of an antibody, an amino acid linker and the CH3 domain of an immunoglobulin molecule.

16. A minibody in accordance with claim 15, wherein said amino acid linker comprises glycine and serine residues.

17. A minibody consisting essentially of (a) a first single chain construct consisting essentially of a light chain variable region joined to a heavy chain variable region which is fused, in sequence, to hinge and CH3 domains of an immunoglobulin molecule, and (b) a second single chain construct consisting essentially of a light chain variable region joined to a heavy chain variable region which is fused to, in sequence, a hinge and CH3 domains of an immunoglobulin molecule, wherein said first single chain construct is linked to said second single chain construct by disulfide bonds between the hinge regions.

18. A minibody consisting essentially of (a) a first single chain construct consisting essentially of a light chain variable region joined to a heavy chain variable region which is fused, in sequence, to a hinge region, an amino acid linker and a CH3 domain of an immunoglobulin molecule, and (b) a second single chain construct consisting essentially of a light chain variable region joined to a heavy chain variable region which is fused, in sequence, to a hinge region, an amino acid linker and a CH3 domain of an immunoglobulin molecule, wherein said first single chain construct is linked to said second single chain construct by disulfide bonds between the hinge regions.

19. The minibody dimer of claim 1, consisting essentially of the light and heavy chain variable domains of the T84.66 CEA antibody fused to hinge and CH3 domains of human IgG.

\* \* \* \* \*

UNITED STATES PATENT AND TRADEMARK OFFICE
CERTIFICATE OF CORRECTION

PATENT NO. : 5,837,821
DATED : November 17, 1998
INVENTOR(S) : Anna M. Wu

It is certified that error appears in the above-identified patent and that said Letters Patent is hereby corrected as shown below:

Title page, item [30], PCT application no. should be --PCT/US92/09347--

Column 3, line 7, " (SEQ ID NO :2)" should be --SEQ ID NO:2 (PKSCDKTHTCPPCGGGSSGGGSGG) --.

Signed and Sealed this

Eleventh Day of January, 2000

Attest:

Q. TODD DICKINSON

*Attesting Officer*    *Acting Commissioner of Patents and Trademarks*